United States Patent
Smith et al.

(10) Patent No.: US 6,506,887 B1
(45) Date of Patent: Jan. 14, 2003

(54) CONDITIONAL-SELEX

(75) Inventors: Jonathan Drew Smith, Boulder, CO (US); Larry Gold, Boulder, CO (US)

(73) Assignee: SomaLogic, Incorporated, Boulder, CO (US)

( * ) Notice: Subject to any disclaimer, the term of this patent is extended or adjusted under 35 U.S.C. 154(b) by 0 days.

(21) Appl. No.: 09/364,541

(22) Filed: Jul. 29, 1999

(51) Int. Cl.[7] .......... C07H 21/02; C07H 21/04; C12Q 1/68; G01N 33/53
(52) U.S. Cl. .......... 536/22.1; 435/6; 435/91.2; 435/7.1; 536/24.3
(58) Field of Search .......... 435/6, 91.2, 7.1; 536/22.1, 24.3; 530/300, 350, 387.1

(56) References Cited

U.S. PATENT DOCUMENTS

| | | | | |
|---|---|---|---|---|
| 5,475,096 A | * | 12/1995 | Gold et al. | 435/6 |
| 5,641,629 A | * | 6/1997 | Pitner et al. | 435/6 |
| 5,723,323 A | | 3/1998 | Kauffman et al. | 435/172.3 |
| 5,731,148 A | * | 3/1998 | Becker et al. | 435/6 |
| 5,741,679 A | | 4/1998 | George et al. | |
| 5,789,163 A | * | 8/1998 | Drolet et al. | 435/6 |
| 5,834,186 A | | 11/1998 | George et al. | |
| 5,849,489 A | * | 12/1998 | Heller | 435/6 |
| 6,214,546 B1 | | 4/2001 | Asher et al. | |

FOREIGN PATENT DOCUMENTS

| | | |
|---|---|---|
| GB | 2 183 661 A | 6/1987 |
| WO | WO89/06694 | 7/1989 |
| WO | WO 91/19813 | 12/1991 |
| WO | WO92/14843 | 9/1992 |
| WO | WO 98/08974 | 3/1998 |
| WO | WO 98/27104 | 6/1998 |
| WO | WO 00/24931 | 5/2000 |
| WO | WO 00/26226 | 5/2000 |
| WO | WO 01/00869 | 1/2001 |
| WO | WO 01/32846 | 5/2001 |
| WO | WO 01/57259 | 8/2001 |
| WO | WO 01/59102 | 8/2001 |
| WO | WO 01/64956 | 9/2001 |
| WO | WO 01/66721 | 9/2001 |

OTHER PUBLICATIONS

Wolfs et al. Biochimica et Biophysica Acta 1172 (1993) 1–4.*
Wiederholt et al. Bioconjugate Chem. 1997, 8, 119–126.*
Hamaguchi, et al. (2001) *Analytical Biochemistry* 294:126–131.
Robertson, et al. (2000) *Nucleic Acids Research* 28:1751–1759.
Robertson, et al. (2001) *Nature Biotechnology* 19:650–655.
Soukup, et al. (1999) *Proc. Natl. Acad. Sci. USA* 96:3584–3589.
Seetharaman, et al. (2001) *Nature Biotechnology* 19:336–341.
Joyce (1989) Gene 82:83.
Joyce & Inoue (1989) Nucleic Acids Research 17:711.
Ellington & Szostak (1990) Abstracts of papers presented at the 1990 meeting on RNA Processing, Cold Spring Harbor Laboratory, Cold Spring Harbor, NY, p. 84.
Kinzler & Vogelstein (1989) Nucleic Acids Research 17:3645.
Kramer et al. (1974) J. Mol. Biol. 89:719.
Levisohn & Spiegelman (1969) Proc. Natl. Acad. Sci. USA 63:805.
Levisohn & Spiegelman (1968) Proc. Natl. Acad. Sci. USA 60:866.
Oliphant et al. (1989) Mol. Cell. Biol. 9:2944.
Oliphant & Struhl (1988) Nucleic Acids Research 16:7673.
Oliphant & Struhl (1987) Methods in Enzymology 155:568.
Oliphant et al. (1986) Gene 44:177.
Robertson & Joyce (1990) Nature 344:467.
Thiesen & Bach (1990) Nucleic Acids Research 18:3203.
Szostak, "Structure and Activity of Ribozymes," in *Redesigning the Molecules of Life*, (S.A. Benner, ed.) Springer–Verlag Berline Heidelberg, pp. 87–113, (1988).

* cited by examiner

*Primary Examiner*—Stephanie Zitomer
(74) *Attorney, Agent, or Firm*—Swanson & Bratschun, LLC

(57) ABSTRACT

The invention provides method for producing nucleic acid ligands that generate a signal, or cause a decrease in the level of a signal, in the presence of a target molecule or an environmental stimulus. The methods of the instant invention are collectively termed Conditional SELEX. The nucleic acid ligands of the instant invention are useful in any application where it is desirable to measure the concentration of a target molecule or detect and quantitate an environmental stimulus.

12 Claims, 5 Drawing Sheets

CONDITIONAL-SELEX

FIELD OF THE INVENTION

This invention is directed to a method for the generation of nucleic acid ligands having specific functions against target molecules using the SELEX process. The present invention provides nucleic acid ligands that undergo a detectable change in the presence of a stimulus. The present invention also provides methods for the isolation of such ligands. The nucleic acid ligands and methods of the instant invention are useful in any application where detection of a target molecule is required.

BACKGROUND OF THE INVENTION

The dogma for many years was that nucleic acids had primarily an informational role. Through a method known as Systematic Evolution of Ligands by EXponential enrichment, termed the SELEX process, it has become clear that nucleic acids have three dimensional structural diversity not unlike proteins. The SELEX process is a method for the in vitro evolution of nucleic acid molecules with highly specific binding to target molecules and is described in U.S. patent application Ser. No. 07/536,428, filed Jun. 11, 1990, entitled "Systematic Evolution of Ligands by EXponential Enrichment," now abandoned, U.S. Pat. No. 5,475,096 entitled "Nucleic Acid Ligands", and U.S. Pat. No. 5,270,163 (see also WO 91/19813) entitled, Methods for Identifying "Nucleic Acid Ligands" each of which is specifically incorporated by reference herein. Each of these applications, collectively referred to herein as the SELEX Patent Applications, describes a fundamentally novel method for making a nucleic acid ligand to any desired target molecule. The SELEX process provides a class of products which are referred to as nucleic acid ligands or aptamers, each having a unique sequence, and which has the property of binding specifically to a desired target compound or molecule. Each SELEX-identified nucleic acid ligand is a specific ligand of a given target compound or molecule. The SELEX process is based on the unique insight that nucleic acids have sufficient capacity for forming a variety of two- and three-dimensional structures and sufficient chemical versatility available within their monomers to act as ligands (form specific binding pairs) with virtually any chemical compound, whether monomeric or polymeric. Molecules of any size or composition can serve as targets in the SELEX method. The SELEX method applied to the application of high affinity binding involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific high affinity nucleic acid ligands to the target molecule.

It has been recognized by the present inventors that the SELEX method demonstrates that nucleic acids as chemical compounds can form a wide array of shapes, sizes and configurations, and are capable of a far broader repertoire of binding and other functions than those displayed by nucleic acids in biological systems.

The basic SELEX method has been modified to achieve a number of specific objectives. For example, U.S. patent application Ser. No. 07/960,093, filed Oct. 14, 1992, now abandoned, and U.S. Pat. No. 5,707,796, both entitled "Method for Selecting Nucleic Acids on the Basis of Structure," describe the use of the SELEX process in conjunction with gel electrophoresis to select nucleic acid molecules with specific structural characteristics, such as bent DNA. U.S. patent application Ser. No. 08/123,935, filed Sep. 17, 1993, entitled "Photoselection of Nucleic Acid Ligands," now abandoned, U.S. Pat. No. 5,763,177 entitled "Systematic Evolution of Ligands by Exponential Enrichment: Photoselection of Nucleic Acid Ligands and Solution SELEX" and U.S. patent application Ser. No. 09/093,293, filed Jun. 8 1998, entitled "Systematic Evolution of Ligands by Exponential Enrichment: Photoselection of Nucleic Acid Ligands and Solution SELEX", now U.S. Pat No. 6,001,577 describe a SELEX based method for selecting nucleic acid ligands containing photoreactive groups capable of binding and/or photocrosslinking to and/or photoinactivating a target molecule. U.S. Pat. No. 5,580,737 entitled "High-Affinity Nucleic Acid Ligands That Discriminate Between Theophylline and Caffeine," describes a method for identifying highly specific nucleic acid ligands able to discriminate between closely related molecules, which can be non-peptidic, termed Counter-SELEX. U.S. Pat. No. 5,567,588 entitled "Systematic Evolution of Ligands by EXponential Enrichment: Solution SELEX," describes a SELEX-based method which achieves highly efficient partitioning between oligonucleotides having high and low affinity for a target molecule.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX process-identified nucleic acid ligands containing modified nucleotides are described in U.S. Pat. No. 5,660,985 entitled "High Affinity Nucleic Acid Ligands Containing Modified Nucleotides," that describes oligonucleotides containing nucleotide derivatives chemically modified at the 5- and 2'-positions of pyrimidines. U.S. Pat. No. 5,580,737, supra, describes highly specific nucleic acid ligands containing one or more nucleotides modified with 2'-amino (2'-$NH_2$), 2'-fluoro (2'-F), and/or 2'-O-methyl (2'-OMe). U.S. patent application Ser. No. 08/264,029, filed Jun. 22, 1994, entitled "Novel Method of Preparation of "Known and Novel 2' Modified Nucleosides by Intramolecular Nucleophilic Displacement," describes oligonucleotides containing various 2'-modified pyrimidines.

The SELEX method encompasses combining selected oligonucleotides with other selected oligonucleotides and non-oligonucleotide functional units as described in U.S. Pat. No. 5,637,459 entitled "Systematic Evolution of Ligands by EXponential Enrichment: Chimeric SELEX," and U.S. Pat. No. 5,683,867 entitled "Systematic Evolution of Ligands by EXponential Enrichment: Blended SELEX," respectively. These applications allow the combination of the broad array of shapes and other properties, and the efficient amplification and replication properties, of oligonucleotides with the desirable properties of other molecules.

The SELEX method further encompasses combining selected nucleic acid ligands with lipophilic compounds or non-immunogenic, high molecular weight compounds in a diagnostic or therapeutic complex as described in U.S. patent application Ser. No. 08/434,465, filed May 4, 1995, entitled "Nucleic Acid Ligand Complexes". Each of the above described patent applications which describe modifications of the basic SELEX procedure are specifically incorporated by reference herein in their entirety.

The central SELEX method for identifying nucleic acid ligands to a target involves (a) contacting the candidate mixture of nucleic acids the target, (b) partitioning between members of said candidate mixture on the basis of affinity to the target, and (c) amplifying the selected molecules to yield a mixture of nucleic acids enriched for nucleic acid sequences with a relatively higher affinity for binding to the target.

In typical embodiments of the SELEX process, the candidate mixture of nucleic acid ligands comprises RNA molecules. Following partitioning step (b) above, the RNA molecules that have higher affinity for the target are reverse transcribed to form a DNA template. This DNA template is then amplified by the Polymerase Chain Reaction (PCR), and the amplified DNA molecules are transcribed in order to provide a new RNA candidate mixture for the next round of the SELEX process.

It is an object of the instant invention to provide nucleic acid ligands that undergo detectable changes in physical properties in the presence of target.

SUMMARY OF THE INVENTION

The present invention provides nucleic acid ligands against target molecules in which the response of a nucleic acid ligand to target or other stimulus is accompanied by a detectable change in some physical property of the nucleic acid ligand. In preferred embodiments, nucleic acid ligands are provided in which the accessibility to solvent of a prosthetic group conjugated to the nucleic acid ligand changes upon binding of the target. Such changes in solvent accessibility result from changes in the conformation of the nucleic acid ligand upon binding the target molecule. This change in the solvent accessibility of the prosthetic group leads to a measurable difference in the properties of the prosthetic group upon binding to target. In some embodiments, the prosthetic group is a fluorophore that undergoes a change in physical properties—e.g., emission spectrum or quantum yield—when its solvent accessibility changes. In other embodiments, the prosthetic group interacts with a ligand in a manner that depends upon the solvent accessibility of the prosthetic group. For example, the prosthetic group can be an inhibitor of an enzyme, and so the activity of the enzyme changes upon binding of target to nucleic acid ligand. In still other embodiments, a nucleic acid ligand is conjugated to an enzyme, and acts as an inhibitor of the enzyme activity conditional upon the presence or absence of the target or stimulus.

The present invention also provides methods for the selection of nucleic acid ligands that have the abovementioned properties. These methods are collectively termed Conditional SELEX. In preferred embodiments, Conditional SELEX exploits the changes in solvent accessibility of the prosthetic group to select nucleic acid ligands in which the prosthetic group is either solvent-accessible or solvent inaccessible in the presence of target. When solvent accessible, the prosthetic group is able to bind to a ligand immobilized on a solid support. Hence nucleic acid ligands that expose a prosthetic group in the presence or absence of target can readily be selected for by virtue of their interaction with the solid support.

DETAILED DESCRIPTION OF THE INVENTION

Definitions

Figure 1A:
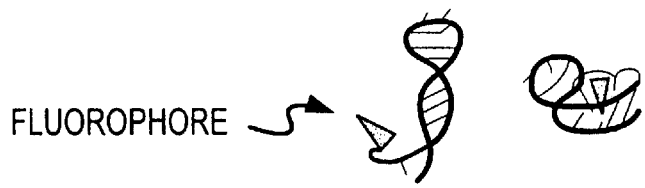
FIG. 1 shows a Conditional SELEX scheme for generating nucleic acid ligands that sequester a fluorophore from the solvent in the presence of target. A candidate mixture, which incorporates a fluorophore (FIG. 1A), is exposed to immobilized antibody directed against the fluorophore (FIG. 1B). The binding target, or other stimulus, is not present. All aptamers which fold so that the fluorophore is accessible to the antibody (and thus to the solvent) are retained. All aptamers which sequester the fluorophore from the antibody are discarded (FIG. 1B). The retained pool of antibody-accessible aptamers is recovered, and mixed with the binding target or otherwise exposed to the stimulus of interest. This mixture is again challenged with the immobilized anti-fluorophore antibody. In this case, the aptamers which have conditionally sequestered the fluorophore are not captured by the antibody, and this fraction is retained for further amplification and selection (FIG. 1C).

Various terms are used herein to refer to aspects of the present invention. To aid in the clarification of the description of the components of this invention, the following definitions are provided:

As used herein, "nucleic acid ligand" is a non-naturally occurring nucleic acid having a desirable action on a target. Nucleic acid ligands are often referred to as "aptamers"; the term "aptamer" is used interchangeably with "nucleic acid ligand" throughout this application. A desirable action includes, but is not limited to, binding of the target, catalytically changing the target, reacting with the target in a way which modifies/alters the target or the functional activity of the target, covalently attaching to the target as in a suicide inhibitor, facilitating the reaction between the target and another molecule. In the preferred embodiment, the action is specific binding affinity for a target molecule, such target molecule being a three dimensional chemical structure other than a polynucleotide that binds to the nucleic acid ligand through a mechanism which predominantly depends on Watson/Crick base pairing or triple helix binding, wherein the nucleic acid ligand is not a nucleic acid having the known physiological function of being bound by the target molecule. Nucleic acid ligands include nucleic acids that are identified from a candidate mixture of nucleic acids, said nucleic acid ligand being a ligand of a given target, by the method comprising: a) contacting the candidate mixture with the target, wherein nucleic acids having an increased affinity to the target relative to the candidate mixture may be partitioned from the remainder of the candidate mixture; b) partitioning the increased affinity nucleic acids from the remainder of the candidate mixture; and c) amplifying the increased affinity nucleic acids to yield a ligand-enriched mixture of nucleic acids.

As used herein, "candidate mixture" is a mixture of nucleic acids of differing sequence from which to select a desired ligand. The source of a candidate mixture can be from naturally-occurring nucleic acids or fragments thereof, chemically synthesized nucleic acids, enzymatically synthesized nucleic acids or nucleic acids made by a combination of the foregoing techniques. In a preferred embodiment, each nucleic acid has fixed sequences surrounding a randomized region to facilitate the amplification process. In preferred embodiments of the instant invention, the candidate mixture is comprised of synthetic RNA molecules that are assembled from smaller RNA fragments.

"SELEX target" or "target" means any compound or molecule of interest for which a ligand is desired. A target can be a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, etc. without limitation.

As used herein, "nucleic acid" means either DNA, RNA, single-stranded or double-stranded, and any chemical modifications thereof. Modifications include, but are not limited to, those which provide other chemical groups that incorporate additional charge, polarizability, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases isocytidine and isoguanidine and the like. Modifications can also include 3' and 5' modifications such as capping. In the instant invention, one preferred modification is the positioning of a methyl group at the 2'-oxygen of ribonucleotides.

"SELEX" methodology involves the combination of selection of nucleic acid ligands which interact with a target in a desirable manner, for example binding to a protein, with amplification of those selected nucleic acids. Optional iterative cycling of the selection/amplification steps allows selection of one or a small number of nucleic acids which interact most strongly with the target from a pool which contains a very large number of nucleic acids. Cycling of the selection/amplification procedure is continued until a selected goal is achieved. The SELEX process is described in U.S. patent application Ser. No. 07/536,428, entitled Systematic Evolution of Ligands by Exponential Enrichment, now abandoned, U.S. Pat. No. 5,475,096 entitled Nucleic Acid Ligands and U.S. Pat. No. 5,270,163 (see also WO 91/19813) entitled Method for Identifying Nucleic Acids Ligands. These patents and applications, each specifically incorporated herein by reference, are collectively called the SELEX Patent Applications.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: (a) to assist in the amplification steps described below, (b) to mimic a sequence known to bind to the target, or (c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained during partitioning.

4) Those nucleic acids selected during partitioning as having the relatively higher affinity for the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The basic SELEX method has been modified to achieve a number of specific objectives. For example, U.S. patent application Ser. No. 07/960,093, filed Oct. 14, 1992, now abandoned, and U.S. Pat. No. 5,707,796 both entitled "Method for Selecting Nucleic Acids on the Basis of Structure," describe the use of the SELEX process in conjunction with gel electrophoresis to select nucleic acid molecules with specific structural characteristics, such as bent DNA. U.S. patent application Ser. No. 08/123,935, filed Sep. 17, 1993, entitled "Photoselection of Nucleic Acid Ligands," now abandoned, U.S. Pat. No. 5,763,177 entitled "Systematic Evolution of Ligands by Exponential Enrichment: Photoselection of Nucleic Acid Ligands and Solution SELEX" and U.S. patent application Ser. No. 09/093,293, filed Jun. 8 1998, entitled "Systematic Evolution of Ligands by Exponential Enrichment: Photoselection of Nucleic Acid Ligands and Solution SELEX" all describe a SELEX based method for selecting nucleic acid ligands containing photoreactive groups capable of binding and/or photocrosslinking to and/or photoinactivating a target molecule. U.S. Pat. No. 5,580,737 entitled "High-Affinity Nucleic Acid Ligands That Discriminate Between Theophylline and Caffeine," describes a method for identifying highly specific nucleic acid ligands able to discriminate between closely related molecules, termed Counter-SELEX. U.S. Pat. No. 5,567,588 entitled "Systematic Evolution of Ligands by Exponential Enrichment: Solution SELEX," describes a SELEX-based method which achieves highly efficient partitioning between oligonucleotides having high and low affinity for a target molecule. U.S. Pat. No. 5,496,938 entitled "Nucleic Acid Ligands to HIV-RT and HIV-1 Rev," describes methods for obtaining improved nucleic acid ligands after SELEX has been performed. U.S. Pat. No. 5,705,337 entitled "Systematic Evolution of Ligands by Exponential Enrichment: Chemi-SELEX," describes methods for covalently linking a ligand to its target.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified nucleic acid ligands containing modified nucleotides are described in U.S. Pat. No. 5,660,985 entitled "High Affinity Nucleic Acid Ligands Containing Modified Nucleotides," that describes oligonucleotides containing nucleotide derivatives chemically modified at the 5- and 2'-positions of pyrimidines. U.S. Pat. No. 5,637,459, supra, describes highly specific nucleic acid ligands containing one or more nucleotides modified with 2'-amino (2'-$NH_2$), 2'-fluoro (2'-F), and/or 2'-O-methyl (2'-OMe). U.S. patent application Ser. No. 08/264,029, filed Jun. 22, 1994, entitled "Novel Method of Preparation of Known and Novel 2' Modified Nucleosides by Intramolecular Nucleophilic Displacement," now abandoned, oligonucleotides containing various 2'-modified pyrimidines.

The SELEX method encompasses combining selected oligonucleotides with other selected oligonucleotides and non-oligonucleotide functional units as described in U.S. Pat. No. 5,637,459 entitled "Systematic Evolution of Ligands by Exponential Enrichment: Chimeric SELEX," and U.S. Pat. No. 5,683,867 entitled "Systematic Evolution of Ligands by Exponential Enrichment: Blended SELEX," respectively. These applications allow the combination of the broad array of shapes and other properties, and the efficient amplification and replication properties, of oligonucleotides with the desirable properties of other molecules.

In U.S. Pat. No. 5,496,938 methods are described for obtaining improved nucleic acid ligands after the SELEX process has been performed. This patent, entitled Nucleic Acid Ligands to HIV-RT and HIV-1 Rev is specifically incorporated herein by reference.

The SELEX process provides a class of products which are nucleic acid molecules, each having a unique sequence, and each of which has the property of binding specifically to a desired target compound or molecule. Target molecules are preferably proteins, but can also include among others carbohydrates, peptidoglycans and a variety of small molecules. SELEX methodology can also be used to target biological structures, such as cell surfaces or viruses, through specific interaction with a molecule that is an integral part of that biological structure.

One potential problem encountered in the diagnostic use of nucleic acids is that oligonucleotides in their phosphodiester form may be quickly degraded in body fluids by intracellular and extracellular enzymes such as endonucleases and exonucleases before the desired effect is manifest. Certain chemical modifications of the nucleic acid ligand can be made to increase the in vivo stability of the nucleic acid ligand or to enhance or to mediate the delivery of the nucleic acid ligand. See, e.g., U.S. patent application Ser. No. 08/117,991, filed Sep. 8, 1993, now abandoned, and U.S. Pat. No. 5,660,985, both entitled "High Affinity Nucleic Acid Ligands Containing Modified Nucleotides", which is specifically incorporated herein by reference. Modifications of the nucleic acid ligands contemplated in this invention include, but are not limited to, those which provide other chemical groups that incorporate additional charge, polarizability, hydrophobicity, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or alkyl phosphate modifications, methylations, unusual base-pairing combinations such as the isobases isocytidine and isoguanidine and the like. Modifications can also include 3' and 5' modifications such as capping.

The modifications can be pre- or post-SELEX process modifications. Pre-SELEX process modifications yield nucleic acid ligands with both specificity for their SELEX target and improved in vivo stability. Post-SELEX process modifications made to 2'-OH nucleic acid ligands can result in improved in vivo stability without adversely affecting the binding capacity of the nucleic acid ligand.

Other modifications are known to one of ordinary skill in the art. Such modifications may be made post-SELEX process (modification of previously identified unmodified ligands) or by incorporation into the SELEX process.

In some embodiments, the nucleic acid ligands become covalently attached to their targets upon irradiation of the nucleic acid ligand with light having a selected wavelength. Methods for obtaining such nucleic acid ligands are detailed in U.S. patent application Ser. No. 08/123,935, filed Sep. 17, 1993, entitled "Photoselection of Nucleic Acid Ligands," now abandoned, U.S. Pat. No. 5,763,177 entitled "Systematic Evolution of Ligands by Exponential Enrichment: Photoselection of Nucleic Acid Ligands and Solution SELEX" and U.S. patent application Ser. No. 09/093,293, filed Jun. 8, 1998, entitled "Systematic Evolution of Ligands by Exponential Enrichment: Photoselection of Nucleic Acid Ligands and Solution SELEX" each of which is specifically incorporated herein by reference in its entirety.

As used herein, "solid support" is defined as any surface to which molecules may be attached through either covalent or non-covalent bonds. This includes, but is not limited to, membranes, columns, plastics, paramagnetic beads, charged paper, nylon, Langmuir-Bodgett films, functionalized glass, germanium, silicon, PTFE, polystyrene, gallium arsenide, gold, and silver. Any other material known in the art that is capable of having functional groups such as amino, carboxyl, thiol or hydroxyl incorporated on its surface, is also contemplated. This includes surfaces with any topology, including, but not limited to, spherical surfaces, grooved surfaces, and cylindrical surfaces.

As used herein, "prosthetic group" refers to any molecule, or grouping of molecules, that can be conjugated to a nucleic acid ligand. Prosthetic groups can be, without limitations: proteins, enzyme inhibitors, enzyme activators, fluorophores, fluorogenic compounds, and antigens.

As used herein, the term "cognate ligand" refers to any molecule that can interact with a prosthetic group. Cognate ligands and prosthetic groups thus form interacting pairs. Without limitation, prosthetic group-cognate ligand pairs include: antigen-antibody pairs, enzyme-enzyme substrate pairs, and biotin-streptavidin pairs.

The present invention provides methods to select aptamers that respond to an experimentally defined condition in such a way as to generate a signal for detection. This condition can be any change in the environment of the aptamer that can cause a change in the conformation or physical properties of the aptamer. Examples of such conditions include, but are not limited to, the presence of the target molecule to which the aptamer binds, changes in pH, ionic strength, light intensity or wavelength, temperature, electromagnetic field, solvent dielectric constant, redox potential, or viscosity. Aptamers can be nucleic acid only, or may be chimeras of nucleic acid and other molecules which may sensitize the aptamer to environmental changes.

Signal generation necessarily involves a change in one or more physical properties of the aptamer. This physical change is used in the instant invention as the basis of the partition which allows useful aptamers to be selected. By combining a selection for the physical change in the presence of the stimulus with a selection for the unchanged state in the absence of the same stimulus, aptamers can be selected which respond specifically to a condition. This selection method is termed Conditional SELEX.

Conditional Availability of a Prosthetic Group

In one embodiment of the invention, one or more prosthetic groups are incorporated into a SELEX candidate mixture in such a way that their ability to interact with a cognate ligand changes upon the binding of a candidate aptamer to a target. Without being bound by a single theory, this difference in the availability of the prosthetic group to its cognate ligand often results when the solvent accessibility of the prosthetic group changes due to a change in the conformation of the aptamer upon binding of its target. If the prosthetic group is buried in the interior of an aptamer, it is not exposed to solvent, and so cannot interact with its cognate ligand. This results in an assayable difference between bound and unbound aptamer; the availability of the prosthetic group depends on the conformation of the aptamer, and is the conditional response of the aptamer.

Any prosthetic group that interacts in an assayable way with its cognate ligand is contemplated in the instant invention. For example, the prosthetic group can be an antigen that can be detected by an antibody only if exposed to the solvent. Alternatively, the prosthetic group may be an inhibitor of an enzyme that only inhibits that enzyme when exposed to the solvent. In some embodiments, the prosthetic group is solvent-exposed only when the aptamer is bound to target; in other embodiments, the prosthetic group is exposed to solvent only when the aptamer is not bound to target. In all cases, assaying for the presence of the prosthetic group can reveal the concentration of the target molecule.

The conditional response of exposing a prosthetic group to its cognate ligand can be easily selected for by the Conditional SELEX process. In general terms, this can be accomplished by partitioning aptamers based on the binding of the prosthetic group to a cognate ligand in the presence or absence of target. For example, in one embodiment of the Conditional SELEX method, a SELEX candidate mixture is synthesized in which a single biotin moiety is incorporated into each candidate nucleic acid ligand. The nucleic acids in this pool will fold in such a way that the biotin is either exposed and available for binding to streptavidin, or the folding will bury the biotin and make it unavailable. These two classes can be resolved by passage over a streptavidin column. For example, a class of aptamers can be selected for in which the biotin is solvent-exposed in the absence of target by passing the candidate mixture over a streptavidin column in the absence of target. Aptamers that do not bind to the column are collected; these aptamers can then passed over a streptavidin column in the presence of target, and aptamers that bind the column are collected. In this way, it is possible to select for aptamers that expose biotin to the solvent, and hence bind to streptavidin, only in the presence of target. These selections can be reiterated as part of the SELEX process until aptamers with the desired affinities and conditional responses are obtained. Here, biotin availability is the conditional response, and can be readily detected through the use of reagents such as streptavidin-alkaline phosphatase.

In some embodiments, assays using the aptamers described above can be performed by conjugating the aptamers to a solid support. The solid support can be incubated with a test mixture suspected of containing a target molecule; the solid support can then be washed and incubated with streptavidin-alkaline phosphatase conjugates. The level of alkaline phosphatase signal is proportional to the concentration of target molecule present in the test mixture.

It will be appreciated by those skilled in the art that the methods described above can be readily adapted to select for aptamers that expose a prosthetic group only in the absence of the target molecule. In the biotin example, aptamers that bind to the streptavidin column in the absence of target are collected, and these aptamers are then passed over the streptavidin column in the presence of target. Aptamers that do not bind to the column in the presence of target are collected, yielding a population of aptamers in which the biotin molecule is available to interact with streptavidin only in the absence of the target. In such cases, the level of prosthetic group exposed to the solvent—measured, for example, by the streptavidin-alkaline phosphatase method if the prosthetic group is biotin—is inversely proportional to the concentration of the target molecule present.

Selection for Conditional Fluorescence Emission Shift

In other embodiments of the invention, the prosthetic group is a fluorophore. It is well known in the art that both the quantum yield and the emission spectrum of fluorophores are affected by the dielectric constant of their immediate environment. Ethidium bromide is a familiar example: its fluorescent quantum yield increases a hundred-fold, and its emission spectrum blue-shifts 15 nm when it moves from the polar environment of an aqueous solvent to a very non-polar environment when intercalated between the bases of a DNA double helix. Fluorescein is another example: it undergoes a 16-fold decrease in fluorescence when shielded from aqueous solvent by antibody binding. Similarly, naphthalein fluorophores experience up to a 7-fold increase in fluorescence when shielded from solvent by intercalation into nucleic acids. Hence, aptamers that are conjugated to a flurophore such that the fluorophore undergoes a change in quantum yield and/or emission spectrum during binding to target are extremely useful reagents.

If a fluorophore moves into the non-polar interior of an aptamer, its inaccessibility to solvent concomitantly renders it inaccessible to potential cognate ligands, such as antibodies directed against it. This inaccessibility can be used as the basis of the Conditional SELEX method.

Figure 1B:
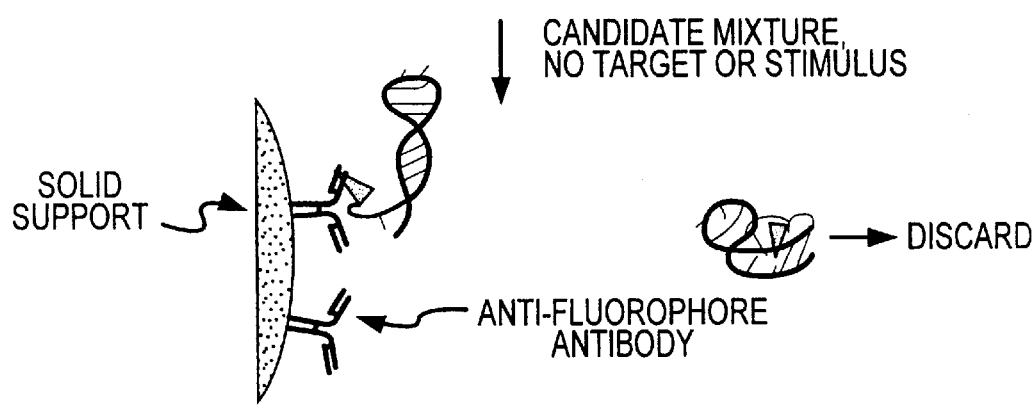

In one embodiment of the invention, a candidate mixture, which incorporates a fluorophore (FIG. 1A), is exposed to immobilized antibody directed against the fluorophore (FIG. 1B). The binding target, or other stimulus, is not present. All aptamers which fold so that the fluorophore is accessible to the antibody (and thus to the solvent) are retained. All aptamers which sequester the fluorophore from the antibody are discarded (FIG. 1B).

Figure 1C:
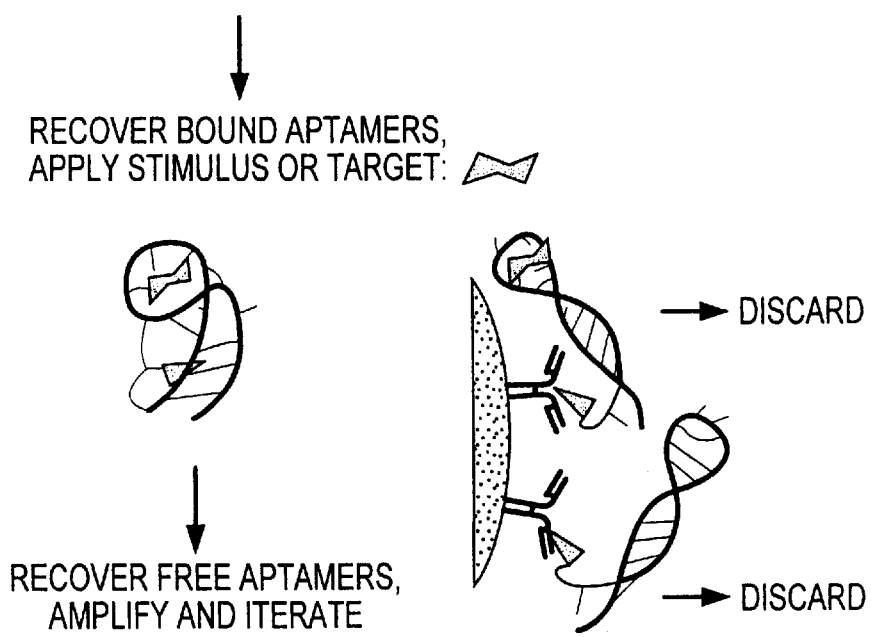

The retained pool of antibody-accessible aptamers is recovered, and mixed with the binding target or otherwise exposed to the stimulus of interest. This mixture is again challenged with the immobilized anti-fluorophore antibody. In this case, the aptamers which have conditionally sequestered the fluorophore are not captured by the antibody, and this fraction is retained for further amplification and selection (FIG. 1C).

After a sufficient number of these paired cycles, the candidate mixture will have become enriched for aptamers which expose fluorophore to solvent in the absence of the target or stimulus, and sequester the fluorophore in the presence of the target or stimulus. The target or stimulus should thus cause a change in the quantum yield and emission spectrum of the fluorophore, which can be used as a signal for its detection.

It will be appreciated by those skilled in the art that this scheme can be reversed, so that aptamers which expose the fluorophore to solvent in the presence of the target or stimulus can also be selected.

Selection for a Conditional Fluorogenic Reaction

Figure 2A:
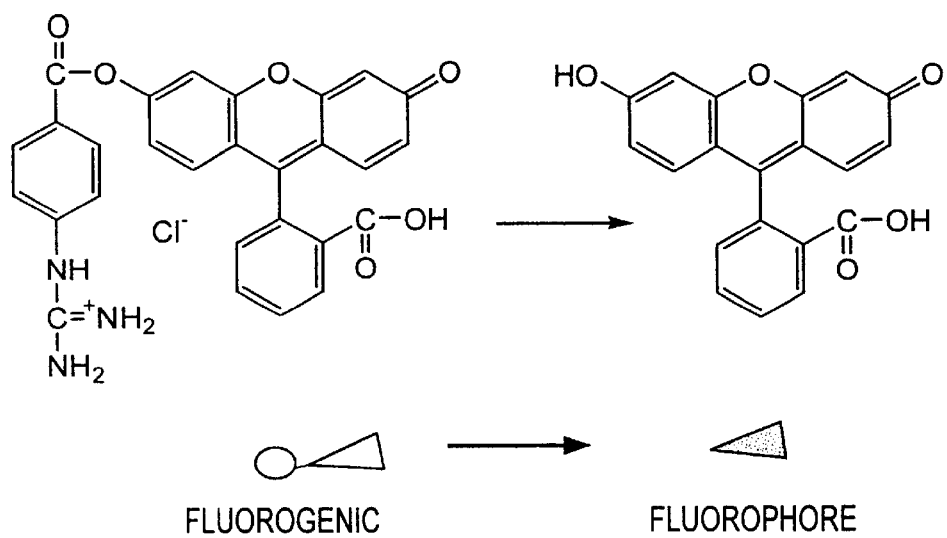
FIG. 2 shows a Conditional SELEX scheme for generating nucleic acid ligands that generate a fluorophore in the presence of target. The fluorogenic precursor and the fluorophore are shown in FIG. 2A. A candidate mixture is created which incorporates the fluorogenic precursor. This candidate mixture is incubated in the absence of the target, to allow any aptamers which spontaneously promote the fluorogenic reaction to do so. The candidate mixture is then exposed to immobilized antibody directed against the fluorophore. This immobilized antibody recognizes only the fluorophore, and not its fluorogenic precursor. The aptamers which promote the fluorogenic reaction are bound to the antibody and discarded (FIG. 2B). The remaining candidate mixture is then mixed with the target or exposed to a stimulus, then partitioned with the anti-fluorophore antibody. Any aptamers which promote the fluorogenic reaction in the presence of the target or stimulus will bind the antibody and be captured. These aptamers have given the desired conditional response, and are retained for further amplification and selection (FIG. 2C).

A number of detection reagents are known in the art which are not themselves fluorescent, but become fluorescent after a covalent reaction, such as bond cleavage or rearrangement. (FIG. 2A). By using an antibody which binds the fluorescent derivative, but not its non-fluorescent precursor, as a partitioning reagent, aptamers can be selected which conditionally perform the fluorogenic reaction. Thus, in general terms, the fluorogenic group acts as a prosthetic group that is modified in such a way that it cannot interact with its cognate ligand. The modified prosthetic group can only interact with its cognate ligand—the antibody—when the modification is removed either through molecular bond cleavage or molecular rearrangement.

Figure 2B:
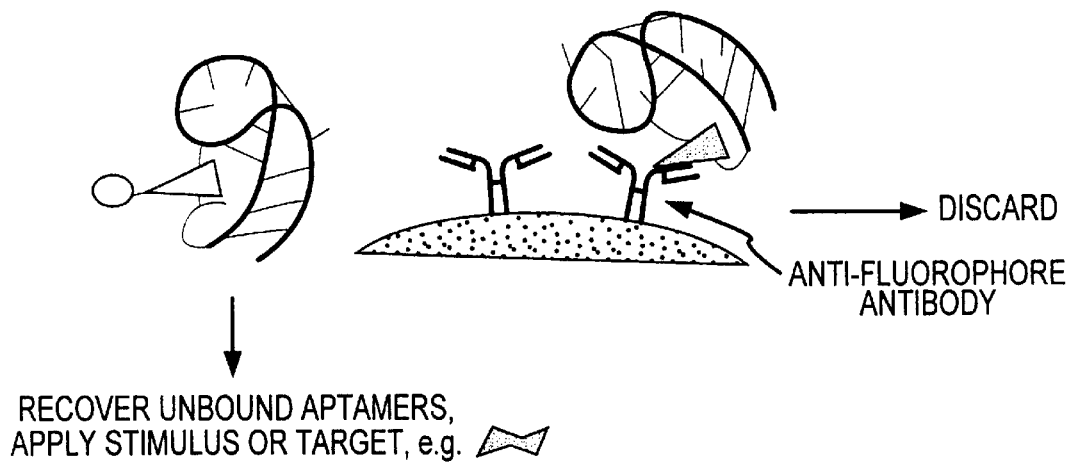
Figure 2C:
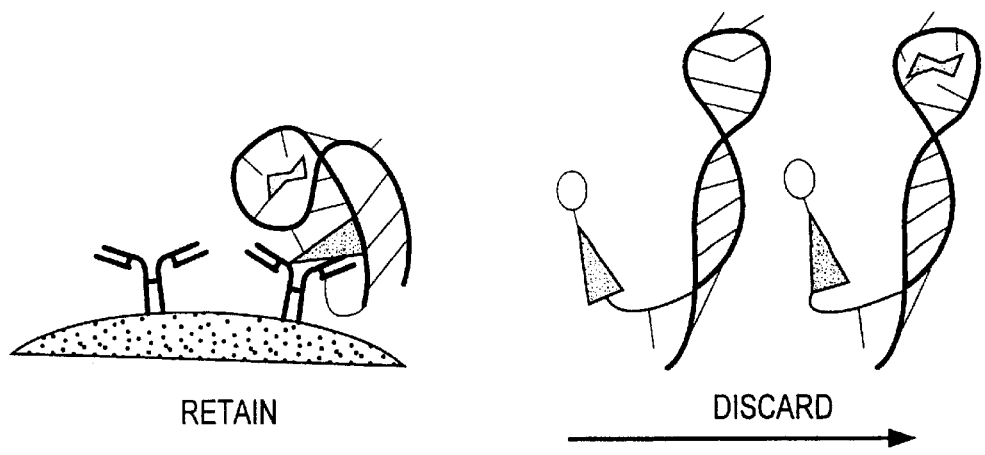

In one embodiment of the invention, a candidate mixture is created which incorporates the fluorogenic precursor. This candidate mixture is incubated in the absence of the target, to allow any aptamers which spontaneously promote the fluorogenic reaction to do so. The candidate mixture is then exposed to immobilized antibody directed against the fluorophore. This immobilized antibody recognizes only the fluorophore, and not its fluorogenic precursor. The aptamers which promote the fluorogenic reaction are bound to the antibody and discarded (FIG. 2B).

The remaining candidate mixture is then mixed with the target or exposed to a stimulus, then partitioned with the anti-fluorophore antibody. Any aptamers which promote the fluorogenic reaction in the presence of the target or stimulus will bind the antibody and be captured. These aptamers have given the desired conditional response, and are retained for further amplification and selection. This results in the selection of aptamers which promote a fluorogenic reaction in response to a target or stimulus. Hence, in the presence of target, such aptamers undergo a great increase in fluorescence emission at the wavelength expected for the fluorophore.

This scheme can be extended to prosthetic groups other than fluorogenic molecules. If the prosthetic group is conjugated to the nucleic acids of the candidate mixture as an inactive derivative—e.g., a prosthetic group that cannot interact with its cognate ligand—, then Conditional SELEX can be performed to select for aptamers in which the derivative becomes active only upon binding of target to the aptamer. For example, in one embodiment, a modified biotin is incorporated into the candidate mixture. This modified biotin is not recognized by biotin-binding cognate ligands, such as streptavidin. Aptamers will be selected which cleave the modification from the biotin in the presence of the target or stimulus. These aptamers can then be bound by streptavidin-fluorescein, or streptavidin-enzyme conjugates, which are used to generate the detection signal.

This scheme can be adapted to generate a positive feedback which will greatly amplify the signal. In this example, the prosthetic group is modified by the target molecule of interest. Conditional SELEX is performed to select for aptamers that bind to the target molecule and then undergo cleavage of the target molecule that is bound to the prosthetic group. Cleavage of the target from the prosthetic group allows the prosthetic group to be detected; furthermore, the released target molecule can then serve, as the target for another aptamer which has not bound its target. For example, a positive feedback system can be designed for the detection of glucose. In this embodiment, the prosthetic group is a fluorophore that has been covalently modified by a glucose group to form a non-fluorescent derivative. This non-fluorescent derivative can then be incorporated into a candidate mixture, and Conditional SELEX can be performed to select for aptamers that bind to glucose, and then undergo conditional cleavage of the glucose-modified fluorophore, releasing another glucose molecule into the solution. This glucose molecule is free to bind another aptamer, which will repeat the reaction, leading to a linear amplification of the signal with respect to time. If aptamers are selected which release 2 or more glucose molecules, the amplification will be exponential.

In the above example, it need not be the case that the amplifying molecule is the same as the target molecule that the system is designed to detect. The aptamer population could be a mixture of two aptamers, one of which senses, one which amplifies. To extend the example of the previous paragraph, the sensing aptamer would be one which releases glucose in response to a change in ionic strength, and the amplification aptamers would be those which release glucose in response to glucose. This scheme allows a single fluorogenic reaction to be used in detecting any experimental condition.

Conditional Coupling of a Signaling Molecule

Figure 3A:
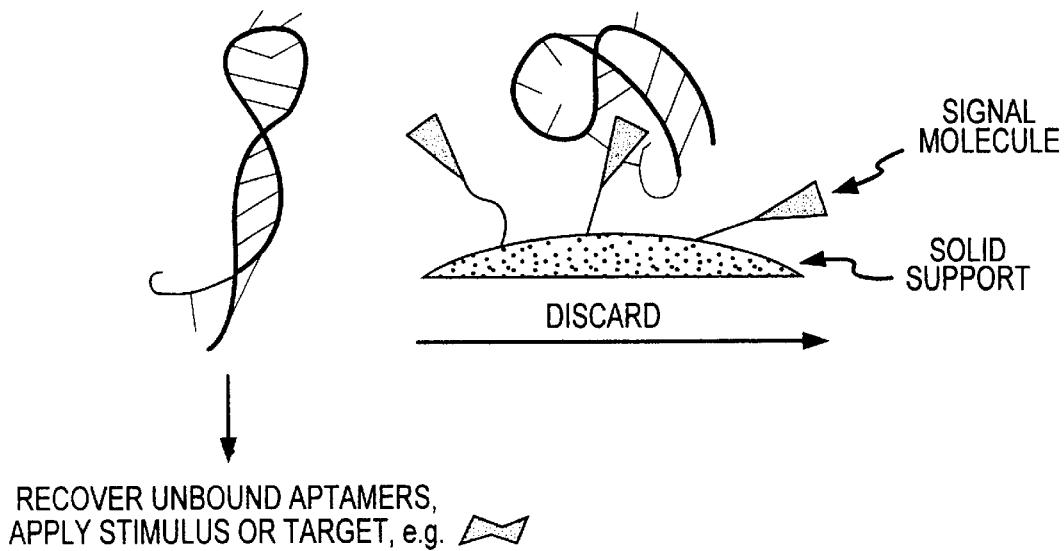
FIG. 3 shows a Conditional SELEX scheme for generating nucleic acid ligands which conditionally capture a molecule which generates a signal. In this example, the nucleic acid ligands capture a signal molecule only when bound to target. The candidate mixture is first exposed to the immobilized signal molecule in the absence of the target or stimulus. Aptamers which capture the signaling molecule in the absence of the target or stimulus are immobilized and discarded (FIG. 3A). If a covalent capture is desired, including capture by photo-activated crosslinking, the library is eluted under denaturing conditions. The candidate mixture is then exposed to the target or stimulus, and again challenged with immobilized signaling molecule. Those aptamers which conditionally bind or react with the signaling molecule are retained, and recovered for further selection and amplification (FIG. 3B). In this way, it is possible to select for aptamers that bind to a signal molecule either in the presence or absence of target.

In other embodiments, aptamers are selected which conditionally capture a molecule which generates a signal. The candidate mixture is first exposed to the immobilized signal molecule in the absence of the target or stimulus. Aptamers which capture the signaling molecule in the absence of the target or stimulus are immobilized and discarded (FIG. 3A). If a covalent capture is desired, including capture by photoactivated crosslinking, the library is eluted under denaturing conditions.

Figure 3B:
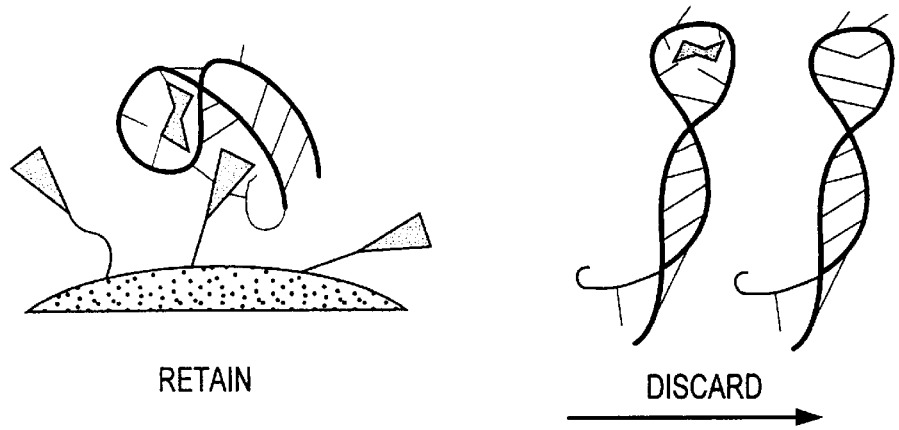

The candidate mixture is then exposed to the target or stimulus, and again challenged with immobilized signaling molecule. Those aptamers which conditionally bind or react with the signaling molecule are retained, and recovered for further selection and amplification (FIG. 3B). In this way, it is possible to select for aptamers that bind to a signal molecule either in the presence or absence of target.

Conditional Generation of Molecular Beacons

The fluorescent emission of one fluorophore (the donor) can be quenched by a second fluorophore (the acceptor) which absorbs in the emission spectrum of the first. This property is well known in the art, and has been exploited in nucleic acid hybridization assays and PCR assays. In these assays, probes are designed which fold to put the fluorophores in close apposition (enabling quenching) in their single-stranded, unhybridized state, and unfold upon hybridizing to form a double-stranded helix, moving the fluorophores and relieving the quench. Conditional SELEX can be used to generate aptamers which cleave off the quenching fluorophore in the presence of a target.

Figure 4A:
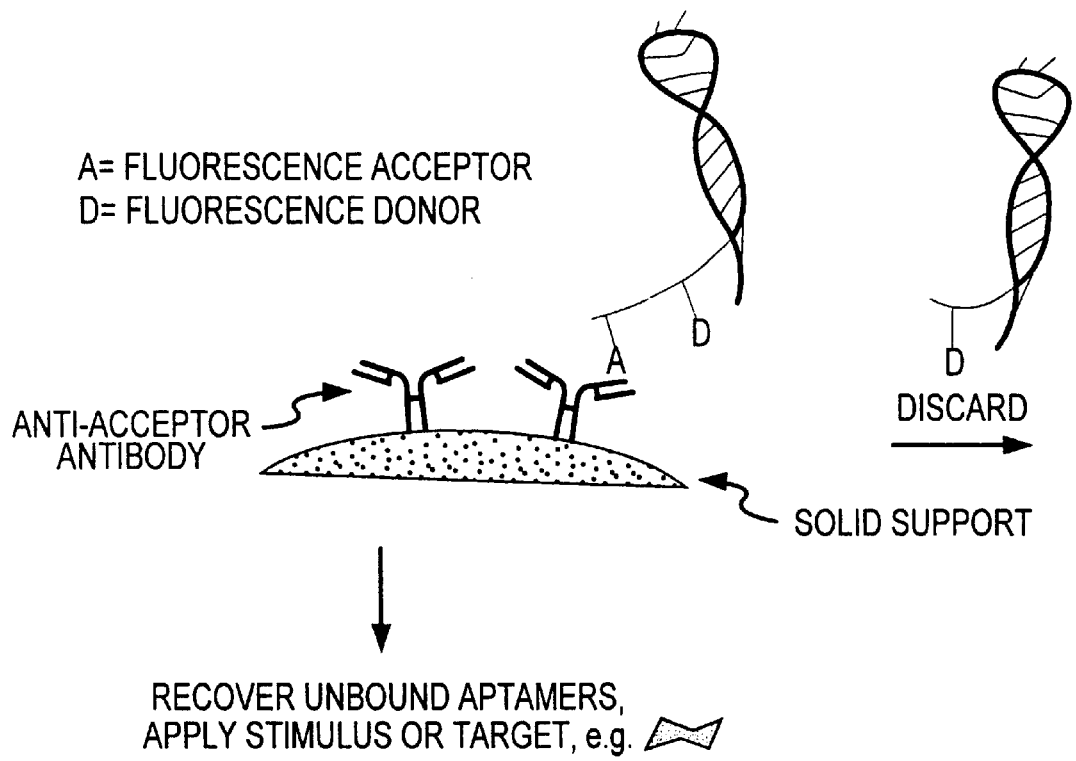
FIG. 4 shows a Conditional SELEX scheme for generating nucleic acid ligands that cleave a fluorescence acceptor molecule from themselves when bound to target. A candidate mixture is constructed which contains the donor-acceptor pair. This is readily done by using a synthetic primer which contains such a pair. In the absence of the target or stimulus, the candidate mixture is mixed with immobilized antibody directed against the acceptor, so that aptamers which cleave the acceptor spontaneously can be discarded (FIG. 4A). The candidate mixture is recovered and exposed to the target or stimulus, and again mixed with immobilized antibody directed against the acceptor. In this case the aptamers which still bind the antibody (and thus retain the acceptor) are discarded (FIG. 4B). Aptamers which have undergone a conditional self-cleavage which releases the acceptor escape capture by the antibody, and are recovered for further amplification and selection.
Figure 4B:
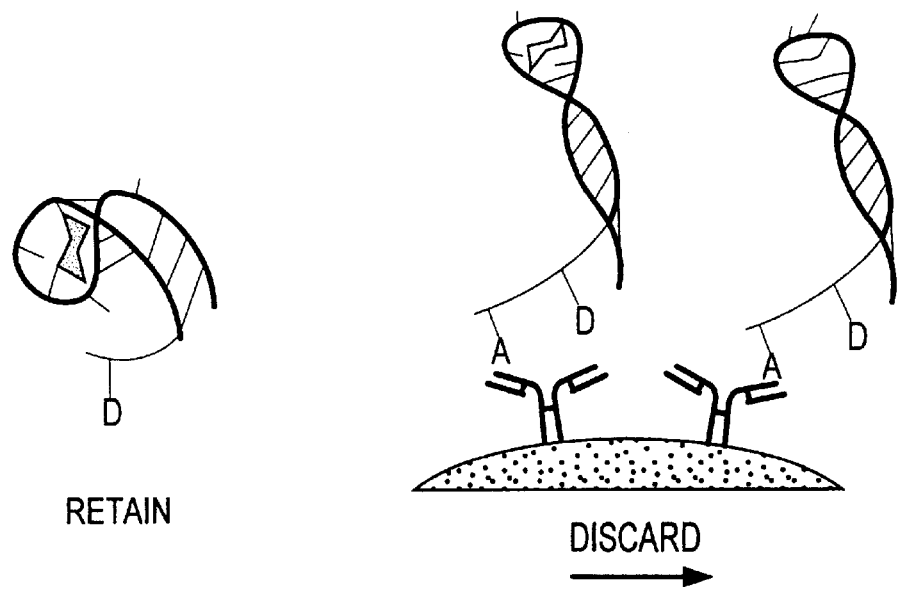

In one embodiment, a candidate mixture is constructed which contains the donor-acceptor pair. This is readily done by using a synthetic primer which contains such a pair. In the absence of the target or stimulus, the candidate mixture is mixed with immobilized antibody directed against the acceptor, so that aptamers which cleave the acceptor spontaneously can be discarded (FIG. 4A). The candidate mixture is recovered and exposed to the target or stimulus, and again mixed with immobilized antibody directed against the acceptor. In this case the aptamers which still bind the antibody (and thus retain the acceptor) are discarded (FIG. 4B). Aptamers which have undergone a conditional self-cleavage which releases the acceptor escape capture by the antibody, and are recovered for further amplification and selection.

Conditional Enzyme-linked Signal amplification

In some embodiments, aptamers are selected which conditionally inhibit the activity of an enzyme to which they are conjugated. The enzyme is one which produces a chemiluminescent, calorimetric, fluorescent, or other signal suitable for diagnostic assays. Because enzyme systems provide an amplified signal—one active enzyme molecule can catalyze the production of many detectable reaction products—such systems provide high sensitivity one-step assays. In general terms, the enzyme acts as a prosthetic group and the substrate acts as the cognate ligand of the enzyme. Conditional SELEX is performed to select for aptamers in which the ability of the enzyme to interact with substrate is conditional on the presence or absence of target.

Figure 5A:
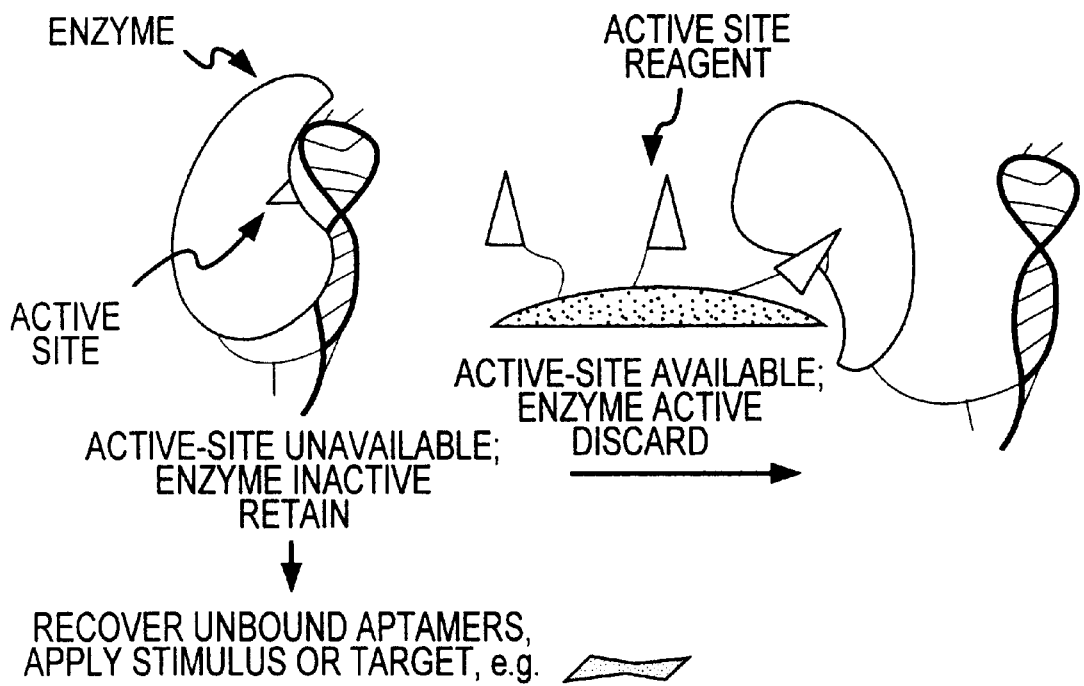
FIG. 5 shows a Conditional SELEX scheme for generating nucleic acid ligand-enzyme chimeras in which the active site of the enzyme is sequestered in the absence of target, but exposed in the presence of target. An enzyme-aptamer chimera candidate mixture is first exposed to an immobilized reagent which binds tightly to the enzyme active site. This reagent can be the enzyme product, a non-cleavable substrate analog, or a mechanism-based inhibitor. In the absence of the target or stimulus, the chimeras which are not retained by the active-site reagent, and thus in which the enzyme is presumed to be inactive because the aptamer is bound to the active site, are recovered (FIG. 5A). This recovered pool is then subjected to the stimulus or target, and again mixed with immobilized active-site reagent. This time the chimeras which are bound to the reagent, and thus in which the enzyme is active in the presence of the stimulus or target, are retained for further selection and amplification (FIG. 5B). The result of this selection will be aptamer-enzyme chimeras which have conditional enzymatic activity.
Figure 5B:
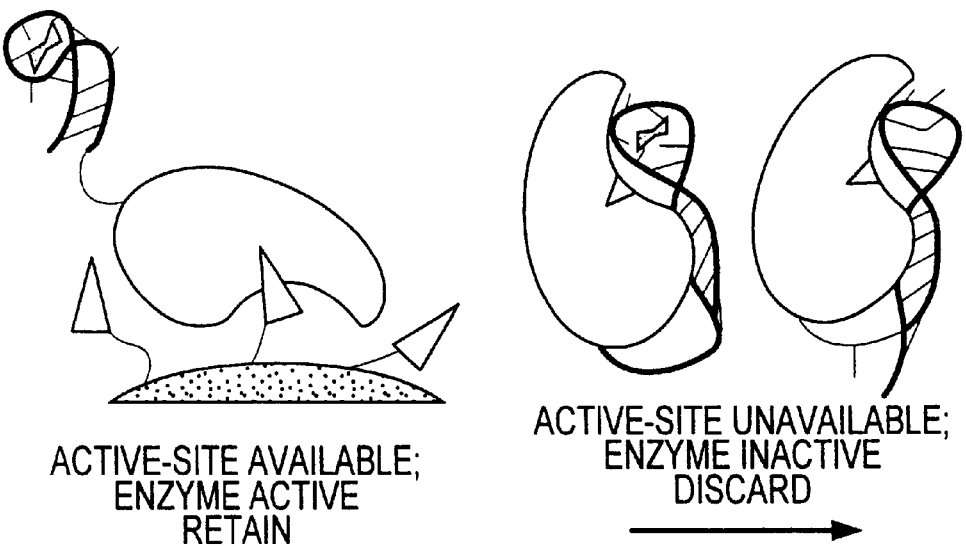

In preferred embodiments, an enzyme-aptamer chimera candidate mixture is first exposed to an immobilized reagent which binds tightly to the enzyme active site. This reagent can be the enzyme product, a non-cleavable substrate analog, or a mechanism-based inhibitor. In the absence of the target or stimulus, the chimeras which are not retained by the active-site reagent, and thus in which the enzyme is presumed to be inactive because the aptamer is bound to the active site, are recovered (FIG. 5A). This recovered pool is then subjected to the stimulus or target, and again mixed with immobilized active-site reagent. This time the chimeras which are bound to the reagent, and thus in which the enzyme is active in the presence of the stimulus or target, are retained for further selection and amplification (FIG. 5B). The result of this selection will be aptamer-enzyme chimeras which have conditional enzymatic activity.

In other embodiments of the invention, each member of the candidate mixture of aptamers is conjugated to both an enzyme molecule and an inhibitor of the enzyme. The enzyme and inhibitor pair are chosen such that the affinity of the inhibitor for the enzyme is high enough that most of the candidate mixture is self inhibited; however, the affinity cannot be so high that the inhibitor will never leave the enzyme. The conditional SELEX is performed using a column that has the inhibitor attached: (1) In the absence of the target, aptamers that do not bind to the column-bound inhibitor are collected. These aptamers are all self-inhibited.

(2) In the presence of the target, aptamers that bind to the column-bound inhibitor are collected. These aptamers are those whose binding of the target pulls the inhibitor away from the enzyme. The result of this SELEX is to generate aptamers in which the enzyme is inhibited in the absence of target, but active in its presence. For example, this scheme can be performed using the enzyme alkaline phosphatase and the inhibitor guanylyl (α,β methylene) diphosphonate. The alkaline phosphatase can be attached to one terminus of the nucleic acids in the candidate mixture by, for example, first conjugating it to a splint sligonucleotide, and then annealing this splint oligonucleotide to the nucleic acids in the candidate mixture. The inhibitor guanylyl (α,β methylene) diphosphonate can be directly conjugated to the nucleic acids in the candidate mixture at the opposite terminus from the enzyme. Following the Conditional SELEX method described above, aptamers can be selected in which alkaline phosphatase activity is present only when the aptamer is bound to target.

Conditional SELEX using an Environmental Stimulus or other Condition

Note that in all the embodiments described above, it is possible to select for aptamers that have a conditional response to an environmental stimulus or other condition, including, but not limited to, changes in pH, ionic strength, light intensity or wavelength, temperature, electromagnetic field, solvent dielectric constant, redox potential, or viscosity. It will be appreciated by those skilled in the art that all the methods described herein for generating target-binding nucleic acid ligands with conditional responses can be easily adapted to generate nucleic acid ligands that have a conditional response to an environmental stimulus or other condition. In general, the steps for enriching for target-binding nucleic acid ligands are omitted, and the conditional response of the nucleic acid ligand—exposing a prosthetic group etc—is selected for in the presence or absence of the environmental stimulus or condition, rather than in the presence or absence of the target. For example, to select for nucleic acid ligands that conditionally expose a prosthetic group to solvent in the presence of an environmental stimulus, the following steps may take place:

a) preparing a candidate mixture of nucleic acids conjugated to said prosthetic group;

b) contacting the candidate mixture of nucleic acids with a solid support conjugated to a cognate ligand of said prosthetic group, wherein nucleic acids in which the prosthetic group is exposed to solvent bind to said cognate ligand;

c) collecting those nucleic acid ligands that do not bind to said cognate ligand on said solid support;

d) contacting, in the presence of said environmental stimulus, the nucleic acid ligands collected at step c) with said solid support conjugated to said cognate ligand;

e) collecting those nucleic acid ligands that bind to said solid support in step d); and f) amplifying the nucleic acids collected at step e) to yield a mixture of nucleic acids enriched for nucleic acids with the conditional response of exposing said prosthetic group to solvent only in the presence of environmental stimulus.

These steps may optionally be repeated until nucleic acid ligands with the desired response are obtained.

What is claimed is:

1. A nucleic acid ligand to a target molecule, the nucleic acid ligand comprising a prosthetic group, wherein the solvent accessibility of said prosthetic group changes upon the binding of said nucleic acid ligand to said target molecule, and wherein said change in solvent accessibility results in a measurable difference in the properties of said prosthetic group.

2. A nucleic acid ligand responsive to an environmental stimulus selected from the group consisting of pH, ionic strength, light intensity, light wavelength, electromagnetic field, solvent dialectric constant, redox potential, viscosity, and temperature, the nucleic acid ligand comprising a prosthetic group, wherein the solvent accessibility of said prosthetic group changes in the response of the nucleic acid ligand to said environmental stimulus, and wherein said change in solvent accessibility results in a measurable difference in the properties of said prosthetic group.

3. A nucleic acid ligand to a target molecule, the nucleic acid ligand conjugated to a prosthetic group, wherein interaction of said prosthetic group with a cognate ligand changes upon binding of said nucleic acid ligand to said target.

4. A nucleic acid ligand responsive to an environmental stimulus selected from the group consisting of pH, ionic strength, light intensity, light wavelength, electromagnetic field, solvent dialectric constant, redox potential, viscosity, and temperature, the nucleic acid ligand conjugated to a prosthetic group, wherein interaction of said prosthetic group with a cognate ligand changes when said nucleic acid ligand is exposed to said environmental stimulus.

5. A nucleic acid ligand to a target molecule, the nucleic acid ligand comprising a fluorophore, wherein the fluorescence emission spectrum or quantum yield of said fluorophore changes upon binding of said nucleic acid ligand to said target molecule.

6. A nucleic acid ligand responsive to an environmental stimulus selected from the group consisting of pH, ionic strength, light intensity, light wavelength, electromagnetic field, solvent dialectric constant, redox potential, viscosity, and temperature, the nucleic acid ligand comprising a fluorophore, wherein the fluorescence emission spectrum or quantum yield of said fluorophore changes when said nucleic acid ligand is exposed to said environmental stimulus.

7. A nucleic acid ligand to a target molecule, wherein the nucleic acid ligand is conjugated to a non-fluorescent fluorogenic group, and wherein said fluorogenic group undergoes intramolecular bond cleavage to generate a fluorescent signal when said nucleic acid ligand binds to said target.

8. A nucleic acid ligand responsive to an environmental stimulus selected from the group consisting of pH, ionic strength, light intensity, light wavelength, electromagnetic field, solvent dialectric constant, redox potential, viscosity, and temperature, wherein the nucleic acid ligand is conjugated to a non-fluorescent fluorogenic group, and wherein said fluorogenic group undergoes intramolecular bond cleavage to generate a fluorescent signal when said nucleic acid ligand is exposed to said environmental stimulus.

9. A nucleic acid ligand to a target molecule, wherein said nucleic acid ligand is conjugated to a prosthetic group, said prosthetic group modified such that it does not interact with a cognate ligand of said prosthetic group, wherein said modified prosthetic group undergoes intramolecular bond rearrangement allowing interaction with said cognate ligand when said nucleic acid ligand binds to said target.

10. A nucleic acid ligand responsive to an environmental stimulus selected from the group consisting of pH, ionic strength, light intensity, light wavelength, electromagnetic field, solvent dialectric constant, redox potential, viscosity, and temperature, wherein said nucleic acid ligand is conjugated to a prosthetic group, said prosthetic group modified such that it does not interact with a cognate ligand of said prosthetic group, wherein said modified prosthetic group undergoes intramolecular bond rearrangement allowing interaction with said cognate ligand when said nucleic acid ligand is exposed to said environmental stimulus.

11. A nucleic acid ligand to a target molecule, wherein said nucleic acid ligand binds to a detectable molecule only when said nucleic acid ligand is bound to said target.

12. A nucleic acid ligand responsive to an environmental stimulus selected from the group consisting of pH, ionic strength, light intensity, light wavelength, electromagnetic field, solvent dialectric constant, redox potential, viscosity, and temperature, wherein said nucleic acid ligand binds to a detectable molecule only when said nucleic acid ligand is exposed to said environmental stimulus.

* * * * *